(12) United States Patent  
Thomas

(10) Patent No.: US 8,048,102 B2
(45) Date of Patent: Nov. 1, 2011

(54) INTERNAL NASAL DILATOR WITH POROUS COMPOUND DELIVERY MATERIAL

(76) Inventor: Brown Thomas, Kansas City, MO (US)

( * ) Notice: Subject to any disclaimer, the term of this patent is extended or adjusted under 35 U.S.C. 154(b) by 1020 days.

(21) Appl. No.: 11/438,267

(22) Filed: May 22, 2006

(65) Prior Publication Data

US 2006/0207598 A1 Sep. 21, 2006

Related U.S. Application Data

(63) Continuation-in-part of application No. 11/065,677, filed on Feb. 24, 2005, now Pat. No. 7,055,523.

(51) Int. Cl.
*A61M 29/00* (2006.01)
(52) U.S. Cl. ...................................................... 606/199
(58) Field of Classification Search .................. 606/191, 606/199; 128/206.11
See application file for complete search history.

(56) References Cited

U.S. PATENT DOCUMENTS

| 4,267,831 | A | * | 5/1981 | Aguilar | 128/203.14 |
| 2004/0059368 | A1 | * | 3/2004 | Maryanka | 606/191 |
| 2004/0116958 | A1 | * | 6/2004 | Gopferich et al. | 606/199 |

* cited by examiner

*Primary Examiner* — Gary Jackson
*Assistant Examiner* — Eric Blatt
(74) *Attorney, Agent, or Firm* — William J. Jacob

(57) ABSTRACT

An internal nasal dilator and compound delivery apparatus preferably includes a U-shaped clip having septum engaging pads, and first and second nostril expanders, wherein the pads engage the septum along planar surfaces, each of the expanders include a conforming outer-nostril wall engaging element and a flexible arm interconnecting the engaging element and clip, and at least a portion of the dilator is formed of a porous material, such as an ethylene vinyl acetate copolymer, configured to retain and discharge over a period a quantity of compound.

19 Claims, 4 Drawing Sheets

INTERNAL NASAL DILATOR WITH POROUS COMPOUND DELIVERY MATERIAL

CROSS-REFERENCES TO RELATED APPLICATIONS

This U.S. Non-Provisional patent application is a continuation-in-part and claims the benefit of U.S. Non-Provisional application Ser. No. 11/065,677 filed on Feb. 24, 2005, now U.S. Pat. No. 7,055,523 entitled INTERNAL NASAL DILATOR AND DELIVERY MECHANISM (hereinafter the 677-Application).

BACKGROUND OF THE INVENTION

1. Field of the Invention

The present invention relates generally to mechanisms and methods for dilating nasal passages and delivering medication, drugs, or other compounds to a user. More particularly, the present invention concerns an improved internal nasal dilator for increasing nasal breathing efficiency and for delivering a compound within the nostrils of a user, over a period.

2. Discussion of the Prior Art

It is well documented that collapsed or constricted nasal passageways result in a multitude of bodily problems, including sleep apnea, sinus infection, and other respiratory ailments. Another well-known problem associated with reduced passageways is snoring. In this condition, audible sounds produced by the vibration of the soft palate and internal nasal structure can be a nuisance to persons within hearing distance and can affect the quality of sleep of the snoring person. Furthermore, it is also known to be desirous to increase the flow capacity of nasal passageways during exercise, athletics, or otherwise strenuous activity.

To alleviate these problems and better achieve these desires, a variety of nasal dilator mechanisms, including external and internal versions, have been developed over time. Prior art external nasal dilators, typically used during athletic or strenuous activity, often take the form of an adhesive strip that is worn on an exterior portion of the nose and function to lift the walls of the nasal passages. Unfortunately, the frictional grab-strength required by these external dilators often causes discomfort or damage to the skin and soft facial tissues of the user. The external placement required of these dilators exposes them to a variety of forces arising from rubbing against objects, such as pillows, that can prematurely dislodge the dilator.

Prior art internal nasal dilators, on the other hand, function within the nostrils of the user, and as a result are not subject to being prematurely dislodged by external forces. These dilators are typically held in place by a clamping mechanism that pinches the septum generally along two contact points, or by stretching the nostrils enough to result in a compressive force on the dilator sufficient to hold it in place. The non-adjustability of these dilators, however, is problematic given that there are an infinite number of sizes and shapes of human nostrils. The pinching mechanisms of these dilators are also problematic in that they cause discomfort to the user, including pain where prolonged usage is necessary. The fact that some of these internal dilators must stretch the nostrils to a greater extent than is necessary to simply dilate the nostril also causes further discomfort and noticeability.

The prior art also includes nasal dilators combined with gaseous or vapor delivery systems for providing a measured flow of medicine to the user. These combinations, however, typically require that an external source be securely connected to the dilator during usage, which makes them problematically cumbersome. Connection to an external source also reduces comfort by limiting the user to certain positions in order to ensure proper operation, which may further inhibit the user from sleeping. Furthermore, these combinations include notoriously complex mechanical, electrical, or pneumatic components that make their manufacture time-consuming and expensive.

U.S. Pat. No. 6,561,188 to Ellis (Ellis '188), for example, discloses an internal dilator having an internal medicine source. In that arrangement, an anti-histamine layer (27) is not attached to an external source, see FIGS. 8A-8E. The layer (27) is attached to other permeable filter layers and overlays the outlet of the nostrils when in place. However, locating the antihistamine near the outlet of the nostrils reduces the effectiveness of delivery and may be wholly inappropriate for other types of medicines, drugs, or compounds because the proximity to ambient air outside the nose results in a measurable percentage of undelivered medicine. Locating the source up-stream from the mucosal lining within the nasal passageway further diminishes the effectiveness of the combination by preventing the administration of medicine during exhalation. Furthermore, the structure of the disclosed mechanism is so large (relative to the volume of the nasal passages) and complex that it may inhibit airflow during normal breathing and may be prohibitively costly to manufacture.

Thus, due to these and other problems and limitations in the prior art, there remains a long felt need for an improved nasal dilator s that dilates the nostrils without substantially restricting the flow of air during respiration, and delivers a desired dosage of compound within the nostrils without extraneous devices or mechanisms.

SUMMARY OF THE INVENTION

The present invention overcomes the problems and limitations in the prior art by providing an improved internal nasal dilator for increasing nasal breathing efficiency and for delivering a time-released compound within the nostrils of a user, and a method of making the same.

A first aspect of the invention concerns an internal nasal dilator adapted for use within a nose having first and second nostrils separated by a septum, with each of the nostrils defining in part an internal nasal passageway and an interior outer wall surface generally opposite the septum. The dilator comprises a generally U-shaped clip configured to contact and apply a holding force to the septum when the dilator is donned. The clip is further configured to contact the septum along first and second planar engaging surfaces. The dilator also includes first and second nostril expanders, wherein each of the expanders further include a nostril engaging element configured to overlay and conform to a portion of the interior outer wall surface of said first or second nostril, and an arm interconnecting the nostril engaging element and clip. The element, arm and clip are cooperatively configured to exert a force upon said portion of the interior outer wall surface.

A second aspect of the invention concerns an internal nasal apparatus that includes a holding element configured to contact and apply a holding force to the nose, so as to secure the apparatus at least partially within the first and second nostrils when the apparatus is donned. The apparatus further includes first and second internal nostril expanders, each connected to the holding element, and configured to exhort an outward force upon the interior outer wall surface, so as to expand the respective nasal passageway. Finally, the apparatus includes a quantity of compound configured to effect an intended response in the user. A novel feature of this aspect of the invention includes at least a portion of the element and expanders being formed of a porous material defining a plurality of interstitial openings configured to retain the compound therein for a period. The expanders, element, compound and material are cooperatively configured, such that the quantity of compound naturally discharges within the respective nasal passageway over the period.

Other aspects and advantages of the present invention will be apparent from the following detailed description of the preferred embodiments and the accompanying drawing figures.

BRIEF DESCRIPTION OF THE DRAWING FIGURES

Several embodiments of the invention are described in detail below with reference to the attached drawing figures, wherein.

DETAILED DESCRIPTION OF THE PREFERRED EMBODIMENTS

With reference to the figures, a nasal dilator, and method of making the same are herein described, shown, and otherwise disclosed in accordance with the preferred embodiments of the present invention. More specifically, the present invention concerns an improved internal nasal dilator for increasing nasal breathing efficiency and for delivering a compound within the nostrils of a user, utilizing porous material composition.

Figure 1A:
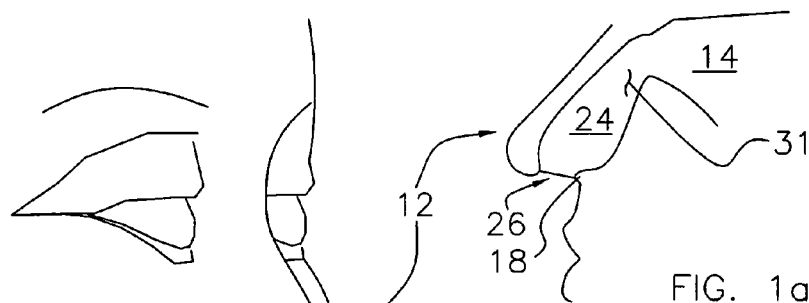
FIG. 1a is a schematic side-elevation view of the innerstructure of the human nose.
Figure 1:
FIG. 1 is a perspective view of an internal nasal dilator constructed in accordance with a first preferred embodiment of the present invention, particularly illustrating the dilator being worn by a user.

As best shown in FIG. 1, a first preferred embodiment of the present invention concerns an improved internal nasal dilator 10 adapted for use predominately within a nose. Although further described herein with respect to a human user, the present invention may be modified in size and shape to properly function within the noses of a variety of animals. For example, the structure of the dilator 10 could be elongated and broadened for equine or canine usage without departing from the present invention. It is also within the present invention to modify the configuration of the dilator, so long as compound storage and delivery occurs at the prescribed minimum distances within the nose.

Figure 1B:
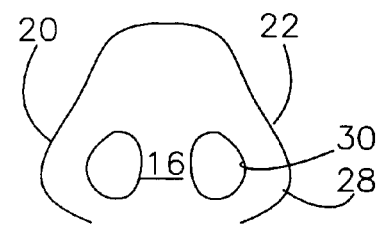
FIG. 1b is an inferior view of the human nose.

Turning first to FIGS. 1, 1a and 1b, the human olfaction organ is divided into an external portion, i.e. the visible projecting portion 12, to which the term "nose" is restricted herein, and an internal portion, consisting of two principal cavities, or nasal fossae 14, separated from each other by a vertical septum 16. Each of the nasal cavities 14 fluidly communicates with ambient air conditions through a constricted orifice, or ostium internum 18, located at the union of the two portions. The nose 12 further presents first and second nostrils 20,22 also separated by the septum 16. Each of the nostrils 20,22 defines in part an internal nasal passageway 24, a nasal outlet 26, and a resistively elastic outer wall 28. The internal nasal passageway 24 as used herein, is limited to the vestibules formed by the nose 12, and does not include the nasal cavities 14 and other inner workings of the organ. The passageway distance is defined as the linear distance along the longitudinal axis of the vestibules as measured from the outlet 26 to the orifice 18. The outer wall 28 presents an interior outer wall surface 30 generally opposite the septum 16. Finally, a mucosal lining 31 further described herein overlays a significant portion of the nasal passageways 24 and cavities 14.

I. First Preferred Structural Configuration of Internal Nasal Dilator

Figure 2:
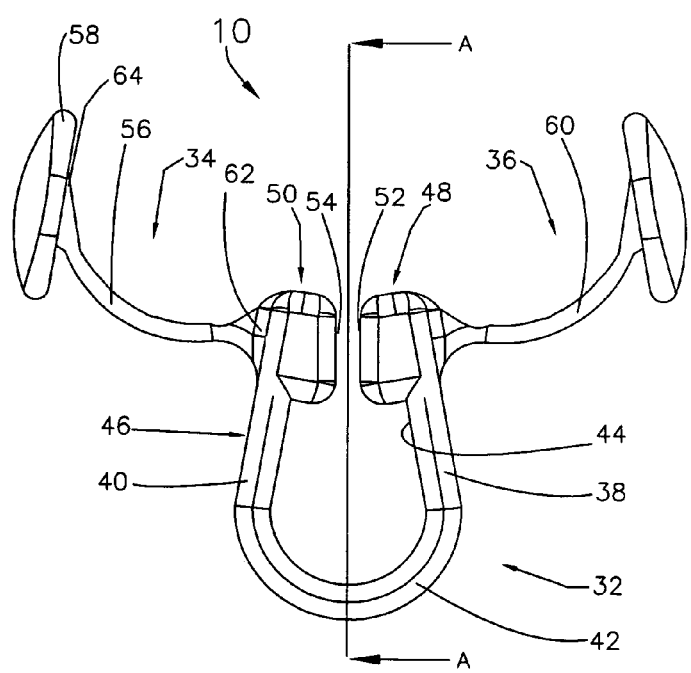
FIG. 2 is a plan view of the dilator shown in FIG. 1 in its normal condition.
Figure 3:
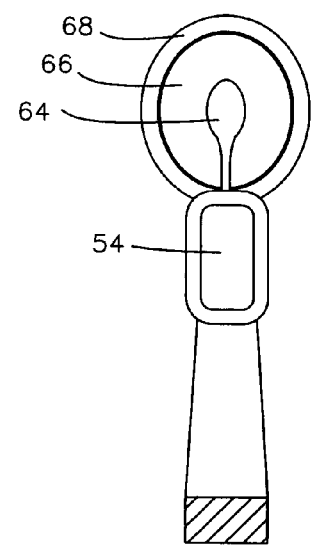
FIG. 3 is a cross-sectional view of the dilator taken along the line A-A shown in FIG. 2, particularly illustrating the connection between the disk and arm.

As best shown in FIGS. 2 and 3, the improved internal nasal dilator 10 includes a septum-constricting clip 32, and left and right nasal expanders 34,36 (i.e., dilating elements). The septum-constricting clip 32 is configured to retain and apply a holding force to a portion of the septum 16. The preferred clip 32 presents a symmetric generally U-shaped body preferably having constant depth and thickness and defining interior and exterior clip surfaces 44,46. The clip 32 is formed by first and second linear portions 38,40 and a bent portion 42 interconnecting the linear portions 38,40. The bent portion 42 is configured so as to place the linear portions 38,40 generally adjacent to the septum 16 by orienting the linear portions 38,40 generally towards the septum 16. Thus, the linear portions 38,40 are configured to converge as they approach their distal ends spaced from the bent portion 42. More preferably, to minimize internal obstruction, at least a section of the linear portions 38,40 present tapered depths, as shown in FIG. 3. In this arrangement, the depth of the clip 32 gradually decreases as the linear portions 38,40 approach their distal ends.

Improved septum engaging pads 48,50 are attached to the clip 32 adjacent the distal ends and along the interior clip surface 44. Each of the pads 48,50 are configured to engage the septum 16 along planar innermost clip surfaces 52,54, so that the septum 16 is not pinched by single point sources of contact during usage. Each of the pads 48,50 presents a trapezoidal shape, wherein the innermost clip surfaces 52,54 are oriented generally parallel to the septum 16 in the normal position (see FIG. 2). More preferably, each of the surfaces 52,54 presents a surface area not less than 0.2 square centimeters, and most preferably, not less than 0.5 square centimeters. Finally, so as not to damage the mucosal lining 31 during placement and removal, the preferred pads 48,50 present chamfered or filleted edges. It is believed that this improved design significantly increases comfort to the user, while stimulating the trigeminal nerve and dilating the nasal passage.

Each of the nasal passage expanders 34,36 are virtually identically configured and, therefore, only nasal passage expander 34 will be described in detail, with the understanding that nasal passage expander 36 is similarly constructed. The expander 34 is configured to retain the outer wall 28 of the nostril 20 in an open or dilated position as shown in FIG. 1. In a first preferred embodiment of the present invention, the expander 34 generally includes an arm 56 spaced from the nostril and a nostril-engaging disk 58 (see FIGS. 2 through 4). By engaging only the interior outer wall surface 30 with the disk 58, the improved expander 34 is configured to minimally engage the nostril 20, thereby reducing noticeability. The arm 56 may present a circular or polygonal lateral cross-section.

More preferably, and as shown in the illustrated embodiment, the arm 56 presents a thin planar body having a first pair of opposite major surfaces 60, and a second pair of parallel surfaces (not shown) generally perpendicular to the first. To reduce obstruction, the preferred arm 56 is oriented such that the major surfaces are parallel with the direction of airflow during respiration. At a first end 62, the arm 56 is fixedly attached to the clip 32 on the outer surface 46 near the distal end of linear portion 40. At the opposite second end 64, the arm 56 is flexibly fixed to the interior surface 66 of the disk 58. The preferred second end 64 presents an oval or circular shape as shown in FIG. 3, which further enables disk 58 flexure. However, other flexible connection configurations may be utilized, including ball-and-socket, without departing from the scope of the present invention. Also shown in FIGS. 2 and 3, the preferred first and second ends 62,64 are enlarged in comparison to the remainder of the arm 56 for increased durability. To facilitate bending, the arm 56 is preferably bowed in an arcuate shape as shown in FIG. 2.

The preferred disk 58 is configured to be comfortably inserted within the nasal passageway 24 and to evenly apply a force therein. The preferred disk 58 presents a thin slightly concave panel. As shown in the illustrated embodiment, the panel is preferably oval in shape. A circumscribing margin 68 extends continuously around the panel and is inverted towards the center of the panel, so as to present a rounded radially outermost disk portion similar to a frisbee. The disk 58 presents a surface area sufficiently sized to engage only a portion of the outer wall 28 of the nostril 20.

The dilator 10 is formed of any suitable non-toxic, hypoallergenic, and bendably rigid natural or synthetic material. More preferably, the dilator 10 is manufactured using a synthetic polymer composition. The selected material and the configuration of the disk 58, however, are preferably configured such that the preferred disk 58 is inelastically bendable and therefore permanently conformable to the shape of the nostril 20. The dilator 10 is preferably constructed through conventional means, such as injection molding, and in a manner that results in seamless contact with the user. At least a portion of the dilator 10, including the septum engaging pads 50,52 and nostril engaging disks 58, can be further molded or double-dipped with a soft rubber material to present a more comfortable outer interface. More particularly, the coating material may comprise of a compressible soft foam, such as a urethane foam approximately 0.025 centimeters thick. A suitable coating may also be utilized to provide other desirable characteristics, such as fluorescence for nighttime viability, scent, or compound delivery as further described herein.

In operation, after selecting a dilator 10 of a suitable size for the user, the dilator 10 is installed by gently bending the expanders 34,36 inward and slightly opening the U-shaped clip) to increase the distance between pads 50,52. The expanders 34,36, linear portions 38,40 of the clip 32, and pads 50,52 are then inserted through the outlets 26 of the nostrils 20,22 and released. The dilator 10 is slid further into the nostrils and adjusted as necessary to reach the desired final location. More preferably, the dilator 10 is maneuvered into place such that the vertex of the bent portion 42 is adjacent the exposed portion of the septum 16 (see FIG. 1). Once in place, the dilator 10 exerts holding and dilating forces upon the nose as it attempts to revert to its normal uncompressed condition shown in FIGS. 2 and 4. More particularly, the expanders 34,36 apply outward biasing forces to the outer walls 28 to maintain the nostrils 20,22 in the open position shown in FIG. 1, and the pads 50,52 compress the septum 16 to help breathing and reduce snoring.

II. Second Preferred Structural Configuration of Internal Nasal Dilator

In a second preferred embodiment of the present invention, dilator 100 is shown with a different configuration, particularly with regard to the expanders 102,104 (see FIGS. 4 through 7). Dilator 100 is preferably similar to dilator 10 in all aspects including material composition, manufacture and modes of operation, except for the following modifications, and, as such, only those aspects of dilator 100 differing from dilator 10 will be further described in detail herein.

Figure 4:
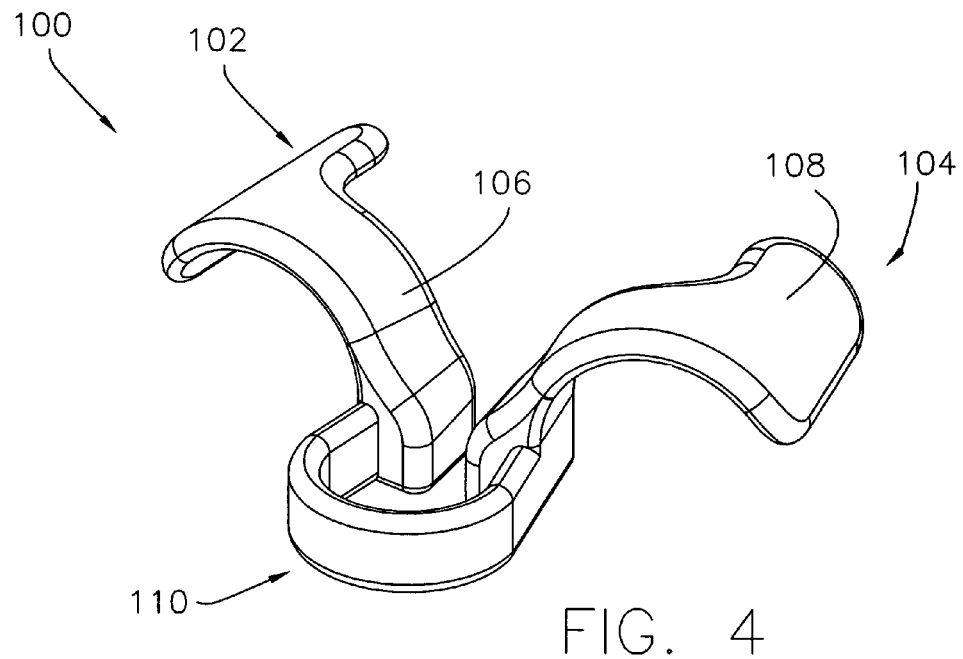
FIG. 4 is a perspective view of an internal nasal dilator constructed in accordance with a second preferred embodiment of the present invention.
Figure 5:
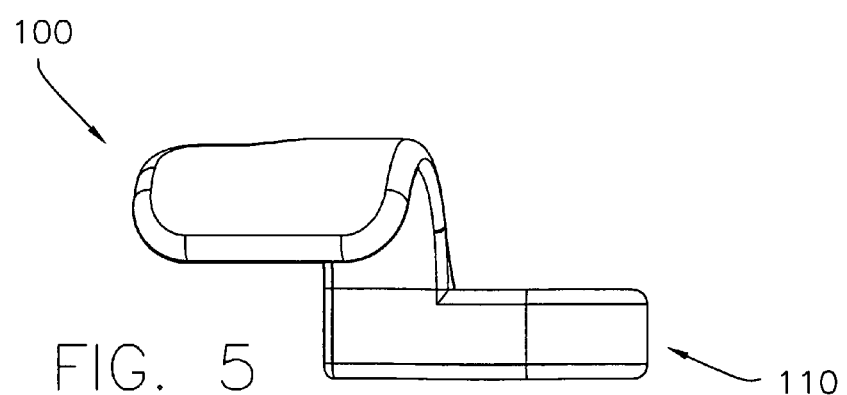
FIG. 5 is a side-elevation view of the dilator shown in FIG. 4.

As shown in FIG. 4, each of the preferably integrally formed expanders 102,104 presents an arm portion 106 spaced from the nostrils 20,22, and a nostril engaging portion 108 adjacent to the distal end of the arm portion 106. Like the expanders 34,36 of the first embodiment, the expanders 102, 104 of the second embodiment preferably present thin planar bodies having first pairs of opposite major surfaces, and second pairs of parallel surfaces perpendicular to the first pairs. The major surfaces of the nostril engaging portions 108 preferably present greater lateral widths than do the major surfaces of the arm portions 106 in order to more broadly apply the dilating force to the nostril. The arm portions 106 are preferably oriented such that the major surfaces are parallel with the direction of airflow during respiration.

Figure 7:
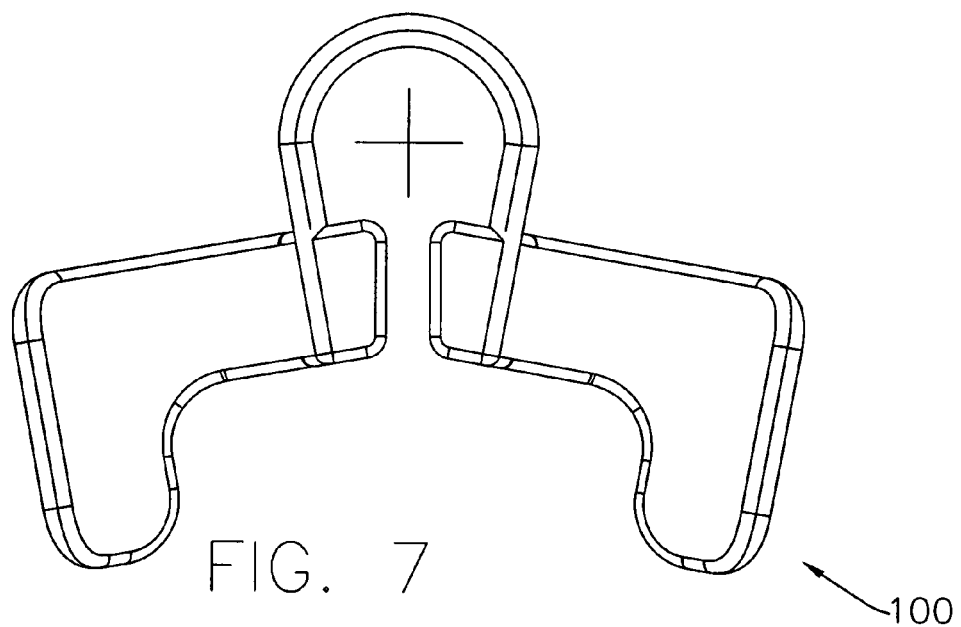
FIG. 7 is a plan view of the dilator shown in FIGS. 4 through 6 in its normal condition, particularly showing the compound delivery elements and septum engaging pads.

As best shown in FIG. 7, the arm portion 106 is fixedly attached to a U-shaped clip 110 similar to the clip 32 of the first embodiment. However, unlike the dilator 10 of the first embodiment, the preferred expanders 102,104 are fixedly attached to the top surface of the linear portions of the clip 110 and pads, and generally project diagonally outward toward two and ten o'clock positions in the normal condition. More preferably, the expanders 102,104 generally project from the top surface of the clip 110 at an approximately forty-five-degree vertical angle from horizontal. It is appreciated that where the flexible outer wall 28 defines a quarter circle between the face and septum 16 of the user, maximum dilation is achieved by orienting the dilating force vector in this direction.

Figure 6:
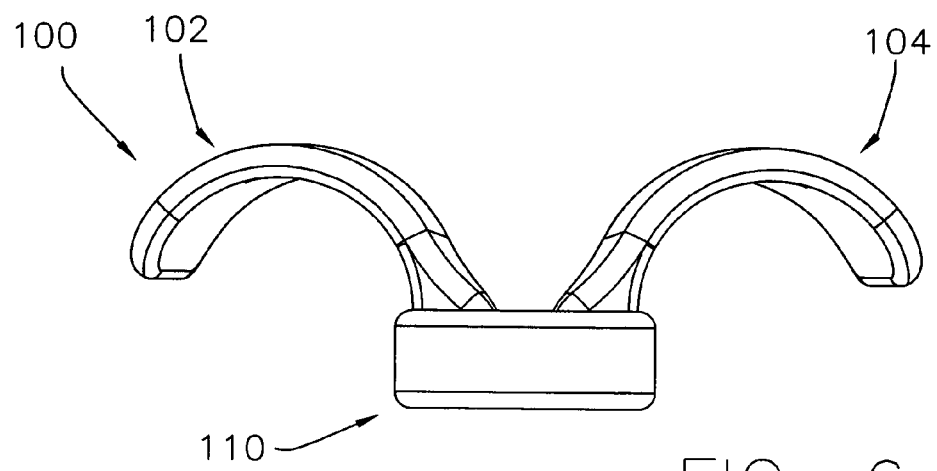
FIG. 6 is a front-elevation view of the dilator shown in FIGS. 4 and 5, particularly showing two compound delivery elements.

The arm portions 106 preferably present upwardly bowed sections so as to promote bending and the application of a biasing force in a bent or flexed condition. As best shown in FIG. 6, the bowed sections more preferably extend along the entire length of the expanders 102,104, so that the expanders 102,104 present half circular or elliptical arcuate elevations. Also shown in FIGS. 4 and 6, the fixed ends of the expanders 102,104 are thicker in comparison to the remainder of the arm portions 106 for increased durability. The fixed end of each expander 102,104 overlays and stems from the full top surface width of a pad and a section of a linear portion of the clip 110 adjacent its distal end. Finally, the dilator 100 preferably presents filleted edges and rounded corners so as to prevent scraping and other damage to the mucosal lining 31 during insertion and removal.

III. Compound Delivery Configuration of Internal Nasal Dilator

Figure 8:
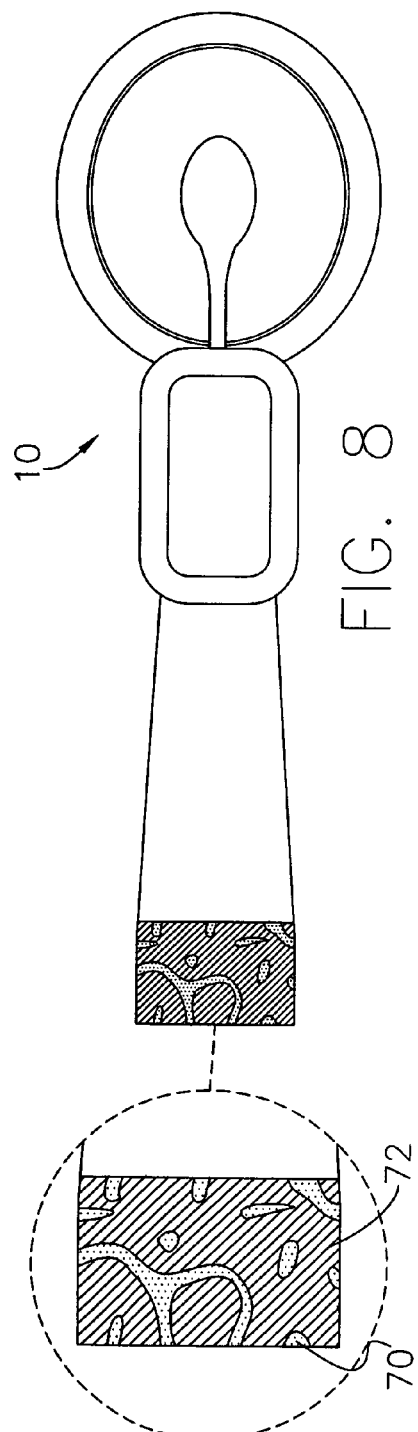
FIG. 8 is a cross-section of the dilator shown in FIGS. 1 through 3, particularly showing a porous material with impregnated or embedded compound.
Figure 9:
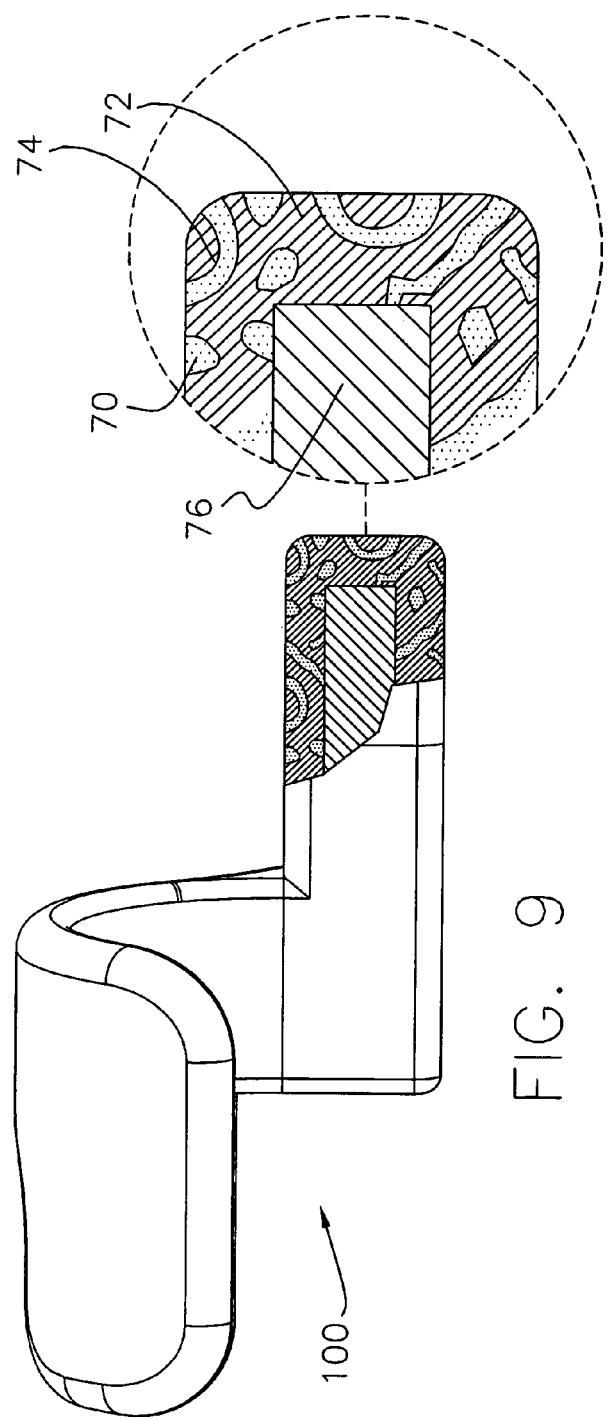
FIG. 9 is a cross-section of the dilator shown in FIGS. 4 through 7, particularly showing an outer layer of porous material and compound coated over a dilator substructure.

As best shown in FIGS. 8 and 9, where delivery of medicine, drugs, or other types of compounds is desired the preferred dilator 10 (this section being equally interchangeable with and applicable to dilator 100) is further configured to store and deliver a quantity of a compound 70 to the mucosal lining 31. As used herein, the term "compound" shall not be given its strict definition in chemistry, but shall include elements, emulsions, suspensions, mixtures and other forms or combinations of substance suitable for use with the present invention. Furthermore, it will be appreciated that the compound may be medicinal or non-medicinal in nature, and may, in that regard, include therapeutic or aromatic substances. More particularly, the compound 70 may comprise of any one or combination of conventional nasal delivery agents, including ionic zinc (as described in U.S. Pat. No. 6,080,783 to Davidson et al.), pain relief agents, antihistamines/decongestants, scenting agents, herbal supplements, insulin, growth hormones, asthma drug medication, germicides, microbicidal agents, and other beneficial agents.

More preferably, the dilator 10 is configured to discharge the compound 70 at a distance not less than twenty-five percent (25%) of the overall nasal passageway length, where it is appreciated that the mucosal lining 31 fully transitions from the outer epidermal. It is also appreciated by those skilled in the relevant art that numerous tiny blood vessels, or capillaries, lie just under the mucosal lining 31 of the nose, near the surface of the nasal passageways, and that delivery of the compound 70 to the lining 31 increases the efficiency of absorption into the blood stream. Most preferably, the dilator 10 is configured to gradually deliver the compound 70 at a distance not less than fifty percent (50%) of total passageway length within the nose, so that compound 70 can also be absorbed by the lining 31 during exhalation.

The compound 70 and dilator 10 are cooperatively configured to discharge the compound 70 over a period. More preferably, the compound 70 is discharged over a period of at least one hour, and, most preferably, over a period within the range of four to twelve hours. In this regard, the preferred dilator 10 is ideally designed for carrying a time-released paste having sufficient viscosity, or a sublimating solid at nasal temperatures, to effect gradual discharge. The paste or solid may alternatively provide for the suspension and delivery of airborne molecules into the passageway 24. It will be appreciated by those in the art that gradually discharging the compound increases the efficiency of absorption into the blood stream, and, therefore, the effectiveness of the active ingredients.

In FIGS. 8 and 9, alternative preferred embodiments of the dilator adapted for compound delivery, and including a porous material 72, are presented. In addition to presenting the necessary flexural strength, flexural modulus, hardness, and tensile strength, the illustrated dilator 10 comprise a material having a minimum porosity (i.e. the fraction of a unit body occupied by space), mean pore size/distribution, and adhesion characteristics, so as to retain and naturally discharge the quantity of compound 70. In this configuration, the dilator 10 presents a plurality of exposed openings defined by a network of interconnected interstitial conduits, minute channels, or pores 74, wherein said pores 74 are inherent to the structure of the material 72, and distinguishable from a borehole, or otherwise formed, machined, or manually produced hole within a body. The entire dilator 10 preferably consists of the material 72. Alternatively, however, only a portion of the dilator 10, such as the engaging disks 58, U-shaped clip 32, or an outer layer of the dilator may consist of the material 72.

With respect to construction, the dilator 10 is preferably pre-formed with material 72, subsequently immersed into pre-set liquid compound, and removed, so that a quantity of compound is allowed to cure, and embed or be impregnated within the pores 74 of the material 72. In this configuration, the material 72 and compound 70 are more preferably cooperatively configured so as to allow the dilator to be re-used after discharge, by re-immersing the dilator 10 in the pre-set liquid compound, and repeating the process.

More preferably, the material 72 and compound 70 are combined prior to formation using a suitable method, such as moulding by extrusion, injection, blow moulding, calendaring or rotational moulding. Most preferably, a porosity inducing treatment is utilized. The mixture preferably solidifies at room temperature, i.e. approximately seventy-three degrees Fahrenheit, and approximately sixty-five percent humidity within a period of four hours. Where desired, a catalyst may be added to the mixture to accelerate the rate of curing, a releasing agent may be added to the mold to facilitate removal of the cast, and a primer, such as maleic anhydride, may be added to facilitate adhesion when coating.

Where the dilator 10 presents a dual layer configuration, it is appreciated that an inner dilator sub-structure 76 may be coated with the material 72 and compound 70, as shown in FIG. 9. To provide the coating, hot molding may be utilized, wherein the compound 70 and material 72 are initially in a solid form, such as pellets or capsules, heated to a sufficient temperature, and allowed to liquefy prior to inserting the sub-structure 76, and a cool-down period is provided to cure the mold. More preferably, a cool-down period of not less than approximately one-hour is provided, while the mixture is exposed to a suitable cooling source (not shown) configured to accelerate the rate of temperature loss.

The preferred material 72 presents porosity and adhesion characteristics to enable a high filler acceptance rate. The material 72 and compound 70 are cooperatively configured so as to release a desired dosage of compound over a period (e.g. 10 to 15 ml/cm$^2$/hr). An exemplary material 72 presenting the necessary flexural capacity, adhesion characteristics, and porosity is an ethylene vinyl acetate (EVA) copolymer of suitable vinyl acetate gradation. It is appreciated by those ordinarily skilled in the art that the level of vinyl acetate included determines characteristics of the copolymer including, but not limited to, the porosity, crystallinity, flexibility, and rigidity of the copolymer, as well as its resistance to salt, water, and other environments. More particularly, a preferred material for use with the present invention is an EVA copolymer containing, but not limited to, a vinyl acetate constituency within the range of 25% to 35%. For example, a 33% vinyl acetate and 73 shore A durometer, or a 28% vinyl acetate and 80 shore A durometer EVA copolymer, may be utilized. One such suitable brand of EVA is Elvax®, made and manufactured by the Dupont corporation, of Wilmington, Del. It is further appreciated that the vinyl acetate gradation may be modified, so as to increase the porosity of the material, and that an increase in porosity results in a larger deliverable dosage, but does not affect the period of delivery. Ethylene butyl resins are also suitable material for use with the present invention. Finally, it is also within the ambit of the invention to utilize other material configured to produce a suitable continuous open-cell structure.

The preferred forms of the present invention and modes of operation described above are to be considered illustrative only, and should not be utilized in a limiting sense in interpreting the scope of the present invention. Obvious modifications to the exemplary embodiments, as set forth above, could be readily made by those skilled in the relevant arts without departing from the spirit of the present invention or the contemplated scope of protection. The inventor hereby states his intent to rely on the Doctrine of Equivalents to determine and assess the reasonably fair scope of the present invention as pertains to any apparatus not materially departing from but outside the literal scope of the invention as set forth in the following claims.

What is claimed is:

1. An internal nasal dilator adapted for use within a nose having first and second nostrils separated by a septum, each of the nostrils defining an internal nasal passageway, and an interior outer wall surface generally opposite the septum, wherein the passageway defines a longitudinal axis, and a cross-sectional plane generally perpendicular to the axis, said dilator comprising:
    a clip configured to contact and apply an inward force to the septum when the dilator is donned, wherein the clip is configured to contact the septum along first and second planar engaging surfaces; and
    first and second nostril expanders, each of the nostril expanders including a nostril engaging engaging element having inner and outer surfaces and configured to overlay only a portion of the interior wall surface of a respective nostril when the dilator is donned, and a compressible arm interconnecting the inner surface of the nostril engaging element and the clip
    wherein the element and clip are interconnected solely by the arm, the arm presents a major axis, a major surface parallel to said major axis, a minor axis perpendicular to the major axis, and a minor surface parallel to the minor axis,
    when the arm is positioned in the nasal passageway, the arm is oriented such that the major axis and major surface extend in a direction that is generally parallel to the longitudinal axis of the nasal passageway, the arm defines a curved longitudinal profile within the cross-sectional plane, and is oriented so as to form superjacent layers with the portion of the outer wall surface,
    the nostril engaging element, arm, and clip are cooperatively configured to exert an outward force upon the portion of the interior outer wall surface, and minimize obstruction within the passageway.

2. The dilator as claimed in claim 1, wherein each of the first and second planar engaging surfaces presents an area not less than 0.25 square centimeters.

3. The dilator as claimed in claim 1, wherein the dilator is generally formed of a substantially synthetic polymer composition.

4. The dilator as claimed in claim 3, wherein at least a portion of the dilator has a soft conformable outer layer.

5. The dilator as claimed in claim 1, wherein the nostril engaging element and the arm are flexibly adjustable.

6. The dilator as claimed in claim 1, wherein the clip and the first and second nostril expanders are integrally formed, so as to present a unitary body.

7. The dilator as claimed in claim 1, wherein the arm presents an arcuately bowed section, so as to conform to a contour defined by the passageway.

8. An internal nasal apparatus adapted for use within the nose of a user, wherein the nose defines first and second nostrils separated by a septum, and each nostril defines in part an internal nasal passageway, an outlet, an internal contour defined by the passageway, a longitudinal axis, a cross-sectional plane generally perpendicular to the longitudinal axis, and an interior outer wall surface generally opposite the septum, the apparatus comprising:
    a holding element configured to contact and apply a holding force to the nose, so as to secure the apparatus at least partially within the first and second nostrils when the apparatus is donned;
    first and second nostril expanders, each connecting to the holding element and including a disk and a planar connection member interconnecting the disk and the holding member, wherein the connection member presents a curved longitudinal profile within the cross-sectional plane of the nasal cavity and conforms to the contour so as to form superjacent layers with the outer wall surface when the dilator is donned, and configured to exert an outward force upon the interior outer wall surface, so as to cause to expand the respective nasal passageway when the apparatus is donned; and
    a quantity of compound configured to effect an intended response in the user,
    at least a portion of said element and expanders being formed of a porous material defining a plurality of interstitial openings wherein the compound is retained,
    said expanders, element, compound and material being cooperatively configured, such that the quantity of compound naturally discharges at a minimum distance within the respective nasal passageway over a predetermined period, when the apparatus is donned.

9. The apparatus as claimed in claim 8, wherein the compound presents a time-release paste, when the dilator is donned.

10. The apparatus as set forth in claim 8, wherein the compound presents a sublimating solid, when the dilator is donned.

11. The apparatus as claimed in claim 8, wherein the period is within the range of four to twelve hours.

12. The apparatus as claimed in claim 8, wherein the holding element includes a U-shaped clip configured to contact and apply a holding force to the septum.

13. The apparatus as claimed in claim 12, wherein each disk defines a free perimeter, and is configured to contact and exert the outward force on a portion of the interior outer wall surface of a respective one of the nostrils.

14. The apparatus as claimed in claim 8, consisting essentially of the compound and material.

15. The apparatus as claimed in claim 8, wherein the material is an ethylene vinyl acetate copolymer.

16. The apparatus as claimed in claim 15, wherein the material is an ethylene vinyl acetate copolymer having a vinyl acetate constituency within the range of 25% to 35%.

17. The apparatus as claimed in claim 8, said expanders, element, compound and material being cooperatively configured, such that the quantity of compound naturally discharges at a dosage rate between 5 to 15 ml/cm.sup.2/hr within the respective nasal passageway over the period, when the apparatus is donned.

18. An internal nasal apparatus adapted for use within the nose of a user, wherein the nose defines first and second nostrils separated by a septum, and each nostril defines in part an outlet, an interior outer wall surface generally opposite the septum, and an internal nasal passageway further defining an interior contour, longitudinal axis, and cross-sectional plane generally perpendicular to the axis, said apparatus comprising:
    a U-shaped clip configured to contact and apply a holding force to the septum, so as to secure the apparatus at least partially within the first and second nostrils, when the apparatus is donned;
    first and second internal nostril expanders, each connected to the clip, and including a disk, and a planar connection member interconnecting the disk and the clip, wherein the connection member presents a curved longitudinal profile within the cross-sectional plane of the nasal cavity and conforms to the contour, so as to form superjacent layers with the outer wall surface when the dilator is donned, and the disk and clip are interconnected solely by the member, said disk and member being cooperatively configured to exert an outward force upon the interior outer wall surface, so as to expand the respective nasal passageway, when the apparatus is donned; and a quantity of compound configured to effect an intended response in the user, at a least a portion of said clip and expanders being formed of an ethylene vinyl acetate copolymer defining a plurality of interstitial openings configured to retain the quantity of compound therein for a period within the range of one to twelve hours, said expanders, element, compound and copolymer being cooperatively configured, such that the quantity of compound naturally discharges within the respective nasal passageway over the period, when the apparatus is donned.

19. The apparatus as claimed in claim 8, wherein each expander includes a nostril engaging element configured to engage the interior outer wall surface, and an arcuate arm interconnecting the holding and nostril engaging elements, and each arm presents a vertically bowed profile so as to generally form superjacent layers with the associated nostril and not bifurcate the associated passageway.

* * * * *